United States Patent [19]

Iyoda

[11] Patent Number: 4,639,831
[45] Date of Patent: Jan. 27, 1987

[54] SENSOR FOR DETECTING AN AMOUNT OF RAIN

[75] Inventor: Motomi Iyoda, Toyota, Japan

[73] Assignee: Toyota Jidosha Kabushiki Kaisha, Japan

[21] Appl. No.: 825,991

[22] Filed: Feb. 4, 1986

[30] Foreign Application Priority Data

Feb. 15, 1985 [JP] Japan .............................. 60-20645[U]
Nov. 29, 1985 [JP] Japan .................................. 60-269830

[51] Int. Cl.$^4$ .......................... H01G 5/20; G01R 27/26
[52] U.S. Cl. .................................... 361/286; 324/61 R
[58] Field of Search ........................ 361/286; 324/61 R

[56] References Cited

U.S. PATENT DOCUMENTS

4,164,868 8/1979 Suntola ............................ 361/286 X
4,429,343 1/1984 Freud .................................... 361/286

Primary Examiner—Donald A. Griffin
Attorney, Agent, or Firm—Parkhurst & Oliff

[57] ABSTRACT

The present invention pertains to a transparent sensor for detecting an amount of rain positioned thereon, which does not prevent the passenger from seeing outside of a vehicle through a window glass. The raid sensor is made from transparent material, and the rain sensor is located within the wiping area on an exterior surface of the window glass. The rain sensor includes a pair of electrodes. One of the pair of electrodes has a plurality of projections, and an interval is defined between each two of the plurality of projections. Another one of the pair of electrodes has a plurality of projections, and an interval is defined between each two of the plurality of projections. Further, the plurality of projections of one of the electrodes are inserted into the interval being defined between each two of the projections of another one of the electrodes. A clearance is defined between the plurality of projections of one of the electrodes and the plurality of projections of another one of the electrodes. Accordingly, the pair of electrodes are insulated electrically by the clearance. An insulating protector film covers the plurality of projections of the electrodes and the clearance, and the insulating protector film is fixed to the plurality of projections of the electrodes and the exterior surface of the window glass. The insulating protector film is made from transparent material.

20 Claims, 12 Drawing Figures

SENSOR FOR DETECTING AN AMOUNT OF RAIN

BACKGROUND OF THE INVENTION

The present invention relates to a sensor for detecting an amount of rain. More particularly, the present invention relates to improvements in the sensor for detecting the amount of rain positioned thereon, which does not prevent a passenger from seeing outside of a vehicle through a window glass.

A conventional sensor for detecting the amount of rain is located on the window glass of the vehicle (e.g. a front windshield), and the conventional sensor can detect the amount of the rain positioned thereon.

However, the conventional sensor is rather thick and is not made from transparent material. Accordingly, the conventional sensor prevents the passenger from seeing the outside. Further, when a wiper wipes out over the conventional sensor which is located on the wiping area of the front windshield, a wiper blade may be impeded in its movement by the thickness of the sensor.

SUMMARY OF THE INVENTION

The present invention was developed in view of the foregoing background and to overcome the foregoing drawbacks. It is accordingly an object of this invention to provide a sensor for detecting the amount of rain positioned thereon, which does not prevent the passenger from seeing the outside of the vehicle through the window glass.

To acquire unimpeded view, the rain sensor is made from transparent material. The rain sensor includes a pair of conductor members. One of the pair of conductor members has a plurality of first projections, and an interval is defined between each two of the plurality of first projections. Another one of the pair of conductor members has a plurality of second projections, and an interval is defined between each two of the plurality of second projections. Further, the plurality of first projections of one of the conductor members are inserted into the interval being defined between each two of the second projections of the other one of the conductor members. Further, a clearance is defined between the plurality of first projections of one of the conductor members and the plurality of second projections of the other one of the conductor members. The pair of conductor members is electrically insulated from one another by the clearance.

An insulating protector member covers the plurality of first and second projections of the conductor members and the insulating protector member is mounted on the plurality of first and second projections of the conductor members, and the clearance defined between the plurality of first and second projections of the conductor members. The insulating protector member is made from transparent material.

BRIEF DESCRIPTION OF THE DRAWINGS

The above objects, features and advantages of the present invention will become more apparent from the description of the invention which follows, taken in conjunction with the accompanying drawings, wherein like reference numerals denote like elements;

FIG. 12 (A) through FIG. 12 (J) are graphs showing relationships of signals of the apparatus shown in FIG. 10 in relation to an output signal outputted from the rain sensor.

DETAILED DESCRIPTION OF THE PREFERRED EMBODIMENT

The present invention will be described in detail with reference to the accompanying drawings which illustrate a preferred embodiment according to the present invention.

Figure 1:
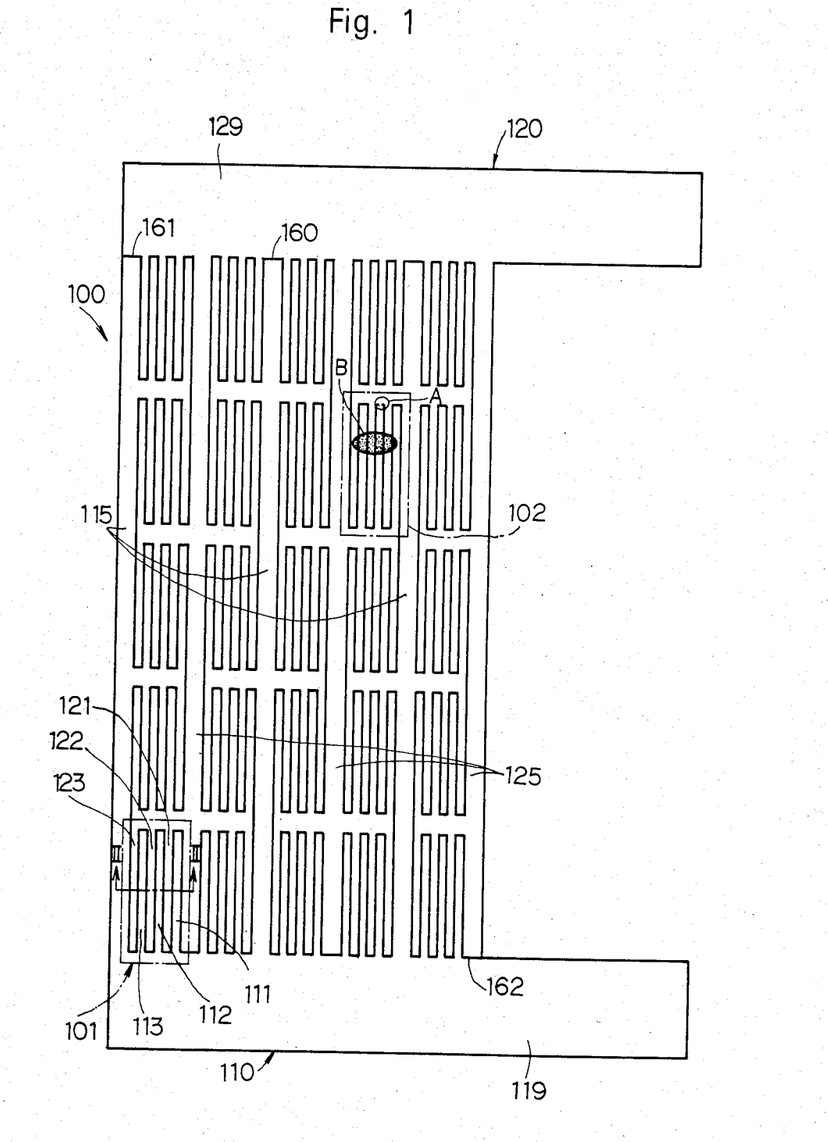
FIG. 1 is a plane view of a rain sensor according to the present invention.

Referring to FIG. 1, a sensor 100 for detecting amount of rain includes a pair of electrodes 110 and 120. The pair of electrodes 110 and 120 are made from transparent material (e.g., ITO film i.e., $In_2O_3(Sn)$). Each of the pair of electrodes 110 and 120 has a thickness of about 0.3 to one micron.

The rain sensor 100 includes a plurality of groups of projections. For explanation, one of the plurality of groups 101 is enclosed by a phantom line. Each group of projections is separated from other groups of projections by wide portions 115 and 125 of the pair of electrodes 110 and 120.

In plurality of groups 101, one of the pair of electrodes 110 has a plurality of projections 111, 112 and 113, and an interval is defined between each two of the plurality of projections (e.g., between the projections 111 and 112). Each projection is about 18 mm in length and about 1.25 mm in width. Another one of the pair of electrodes 120 has a plurality of projections 121, 122 and 123, and an internal is defined between each two of the plurality of projections (e.g., between the projections 121 and 122). Each projection is about 18 mm in length and about 1.25 mm in width.

The plurality of projections 111, 112 and 113 of one of electrodes 110 are inserted into the interval being defined between each two of the projections 121, 122 and 123 of the other electrodes 120. A clearance 160 is defined between the plurality of projections 111, 112 and 113 of electrode 110 and the plurality of projections 121, 122 and 123 of electrode 120. The clearance 160 is abot 0.1 through 0.3 mm in width, and the clearance 160 is continuous from 161 to 162. Accordingly, the pair of electrodes 110 and 120 are physically separated and electrically insulated from each other by the clearance.

Figure 2:
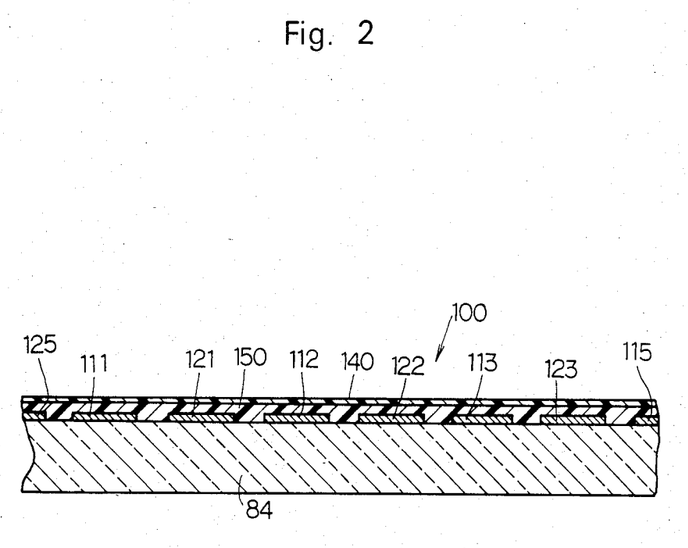
FIG. 2 is an enlarged cross-sectional view of a portion of the rain sensor taken along the line II—II in FIG. 1.

As shown in FIG. 2, the pair of electrodes 110 and 120 are fixed to an exterior surface of the windshield 84 by vacuum evaporation, spattering or ion plating.

An insulating protector film 150 covers the electrodes 110 and 120 an the insulating protector film 150 is fixed to the electrodes 110 and 120 and the exterior surface of the windshield 84 defining between the electrodes 110 and 120 by ion plating, vacuum evaporation or spattering. The insulating protector film 150 is made from transparent material (e.g., alumina ($Al_2O_3$), Zirconia ($ZrO_2$) or silica ($SiO_2$)) and the insulating protector film 150 has a thickness of about one fifth micron through 0.3 micron on the electrodes 110 and 120. The transparent materials are of materials which insulate electrically between the electrodes 110 and 120.

Further, a coat film 140 covers an exterior surface of the insulating protector film 150 and the coat film 140 is fixed to the insulating protector film 150 by ion plating, vacuum evaporation or spattering. The coat film 140 is also made from transparent material (e.g., Alumina ($Al_2O_3$), Zirconia ($ZrO_2$) or Silica ($SiO_2$)) and the coat film 140 has a thickness of about 0.1 through 0.3 micron on the insulating protector film 150. The combination of materials of the insulating protector film 150 and the coat film 140 is determined in order to prevent light from reflecting on the coat film 140. (e.g., when the insulating protector film 150 is made from Alumina ($AL_2O_3$), the coat film 140 is made from Silica ($SiO_2$), when the insulating protector film 150 is made from Zirconia ($ZrO_2$), the coat film 140 is made from Alumina ($Al_2O_3$) or Silica ($SiO_2$) or when the insulating protector film 150 is made from Silica ($SiO_2$) the coat film 140 is made from Alumina ($Al_2O_3$).)

Accordingly, the rain sensor 100 has the above mentioned structure and is made from the above mentioned materials, so that the rain sensor 100 is very thin, because each of the electrodes 110 and 120, the insulating protector film 150 and the coat film 140 has thickness of below one micron. Further, the electrodes 110 and 120 are well protected from impact and are insulated electrically each other by the insulating protector film 150 and the coat film 140.

Figure 3:
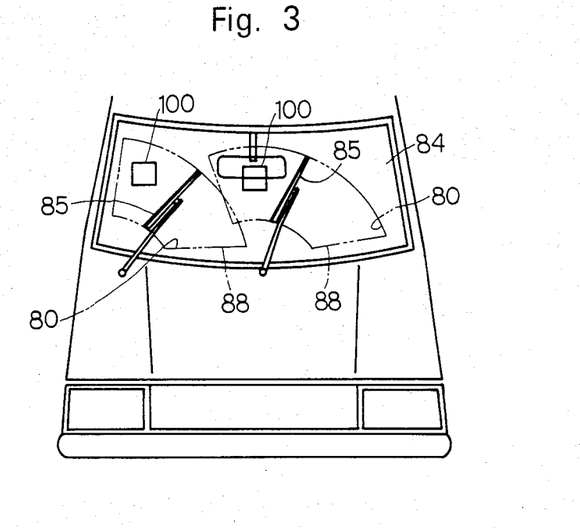
FIG. 3 is a front view of a vehicle, in which the rain sensor is located on a windshield of the vehicle.

Referring to FIG. 3, when a wiper 85 wipes out a wiping area 80, the rain sensor 100 does not become an obstacle to prevent the movement of the wiper 85, so that a blade of the wiper 85 is not damaged by the rain sensor 100. Further, the coat film 140 is fixed to the insulating film 150, so that the coat film 140 prevents the light from reflecting on the insulating protector film 150. As a result, as a whole the transparency of the rain sensor 100 improves.

As shown in FIG. 3, the rain sensor 100 is located on an exterior surface of the front windshield 84 of the vehicle and the rain sensor 100 detects amount of rain which is positioned on the rain sensor 100. The rain sensor 100 outputs a continuous signal. The wiper 85 wipes out the wiping area 80 defined on the exterior surface of the front windshield 84 and the wiper 85 moves from and returns to an initial position 88 which is located at the lowest position of the wiping area 80 so that when the wiper 85 stops its movement the wiper 85 is positioned at the initial position 88 and is not an obstacle which prevents occupants from seeing the outside of the vehicle through the front windshield 84. The rain sensor 100 is located in the vicinity of an apex of movement of the wipers 85 within the wiping area 88.

Figure 4:
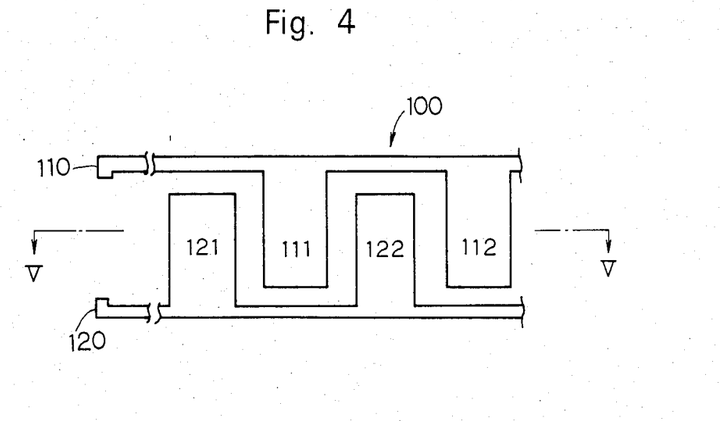
FIG. 4 is an enlarged explanatory plane view of the portion of the rain sensor.
Figure 5:
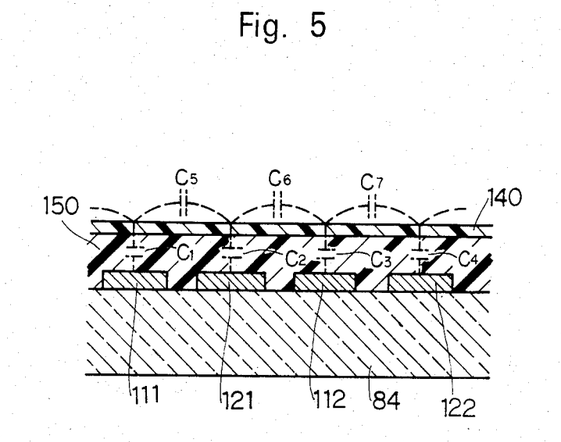
FIG. 5 is an enlarged explanatory cross-sectional view of the portion of the rain sensor taken along the line V—V in FIG. 4.

Referring to FIGS. 4 and 5, one of the pair of electrodes 110 has the plurality of projections 111 and 112 and an interval is defined between each two of the plurality of projections 111 and 112. Another one of the pair of electrodes 120 has the plurality of projections 121 and 122, and the interval is defined between each two of the plurality of projections 121 and 122. The plurality of projections 111 and 112 of electrode 110 are inserted into the interval being defined between each two of the projections 121 and 122 of electrode 120, but the plurality of projections 111 and 112 of the electrode 110 and the plurality of projections 121 and 122 of electrode 120 do not touch. The pair of electrodes 110 and 120 are electrically insulated by the clearance. Further, the insulating protector film 150 covers the electrodes 110 and 120 and the insulating protector film 150 is fixed to the electrodes 110 and 120 and the exterior surface of the windshield 84, so that the pair of electrodes 110 and 120 are securely electrically insulated by the insulating protector film 150.

Figure 6:
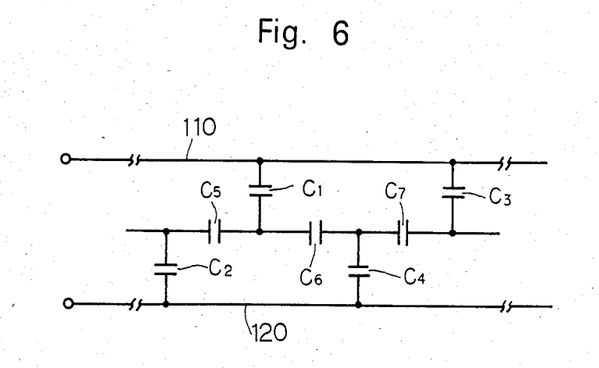
FIG. 6 is an explanatory circuit illustrating an equivalent network to the rain sensor in FIG. 5.

As a result, the rain sensor 100 forms a plurality of floating capacitors $C_1$ through $C_7$ between the electrodes 110 and 120 as shown in FIGS. 5 and 6. FIG. 6 is an explanatory circuit illustrating an equivalent network to the rain sensor in FIG. 5.

The floating capacitors $C_1$, $C_5$ and $C_2$ are formed between the projections 111 and 121 of the electrodes 110 and 120, the floating capacitors $C_2$, $C_6$ and $C_3$ are formed between the projections 121 and 112 of the electrodes 120 and 110, and the floating capacitors $C_3$, $C_7$ and $C_4$ are formed between the projections 112 and 122 of the electrodes 110 and 120.

The floating capacitors $C_5$, $C_6$ and $C_7$ are of variable capacitance and when a drop of water positions at a portion of the coat film 140 defined between the projections 111 and 121 of the electrodes 110 and 120, a varied capacitance of the floating capacitor $C_5$ becomes greater than a normal capacitance of the floating capacitor $C_5$ because the dielectric constant of the drop of water is greater than the dielectric constant of air. Accordingly, when many drops of water postion on the coat film 140, the total capacitance formed between the electrodes 110 and 120 become larger. Further, the total capacitance is approximately in proportion to the number of drops of water (i.e., the amount of rain) positioned on the coat film 140.

Figure 7:
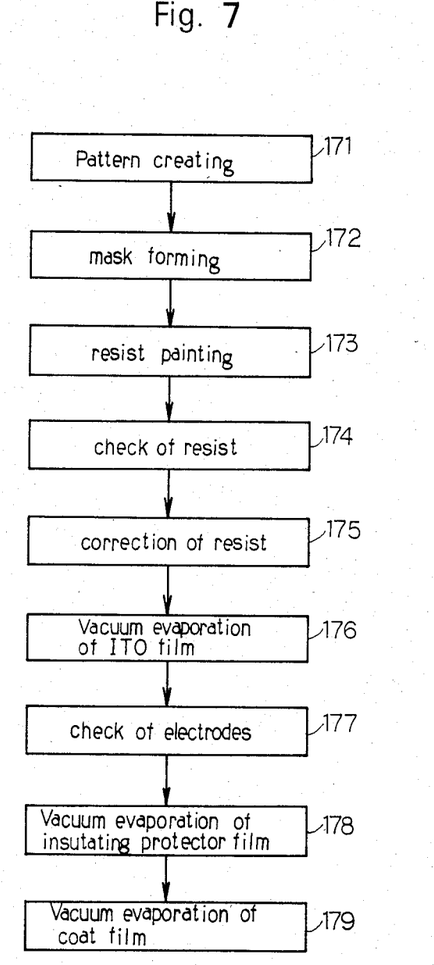
FIG. 7 is a block diagram showing a process of manufacturing the rain sensor.

FIG. 7 shows a block diagram illustrating the manufacturing process of the rain sensor 100. During the manufacturing process, a pattern is created in first step 171, and a mask is formed on the basis of the pattern in second step 172. The mask can cover all projections (e.g., 111 through 113 and 121 through 123), the wide portions 115 and 125, and terminal portions 119 and 129 of the pair of electrodes 110 and 120. In third step 173, the mask is fixed to the exterior surface of the windshield 84 and then the resist is painted on both the exterior surface of the windshield 84 and the mask, and in fourth step 174, the mask is removed from the windshield 84 and a remainder of the resist is checked.

The remainder of the resist corresponds to the clearance 160. As shown by "A" in FIG. 1, if an inspector finds a break in the remainder of the resist, the remainder of the resist is corrected in fifth step 175. If a break is kept in the remainder of the resist and then the transparent material is fixed to the windshield, the electrodes 110 and 120 would not be insulated from each other so that as a whole the rain sensor 100 would not work.

Therefore, a break in the remainder of the resist should be found, and corrected carefully.

However, the rain sensor 100 according to the present invention includes the plurality of groups of the projections (e.g. 101 or 102 in FIG. 1), each of which is defined and separated by the wide portions 115 and 125, so that one of group of projections 102 is corrected by painting the resist on group of projections 102 regardless of the position of the break on the reminder of the resist as shown by "B" in FIG. 1. It is easy for the corrector to correct the remainder of the resist by the above mentioned method of correction, because the correction of the above mentioned way does not require much time or attention. However, according to the method of the correction mentioned above, the one group of projections 102 does not work as a part of rain sensor 100.

However, the rain sensor 100 has a plurality of groups of projections, so that as a whole the rain sensor 100 can detect the amount of rain positioned thereon.

In sixth step 176 of the manufacturing process, the transparent material (e.g. $In_2O_3(Sn)$) is fixed to the exterior surface of the windshield 84 and the resist by vacuum evaporation, and then the resist and the transparent material fixed on the resist are removed from the exterior surface of the windshield 84. As a result, the pair of electrodes 110 and 120 which are made from the transparent material are securely fixed to the windshield 84 as shown in FIG. 1. The pair of electrodes 110 and 120 are electrically insulating from each other by the clearance 160.

Further, in seventh step 177, the pair of electrodes 110 and 120 are checked electrically, and then in a step 178 the insulating protector film 150 is fixed to the exterior surface of the windshield 84 and the pair of electrodes 110 and 120 by vacuum evaporation.

Finally, in eight step 178, the coat film 140 is fixed to the insulating protector film 150 by vacuum evaporation.

Figure 8:
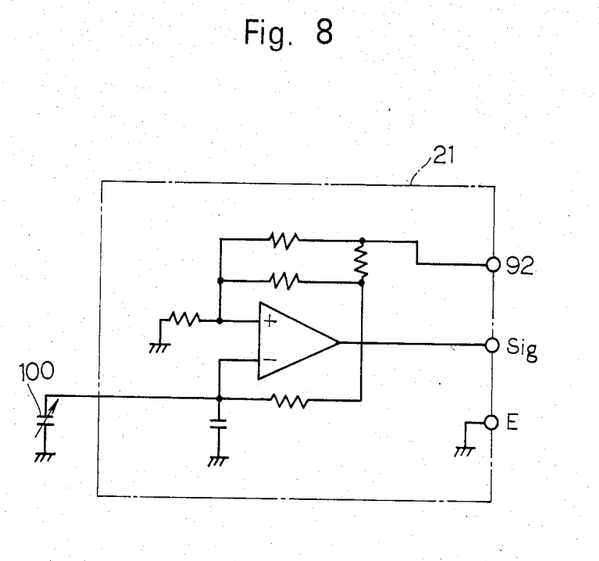
FIG. 8 is a schematic circuit illustrating an oscillator connected to the rain sensor.
Figure 9:
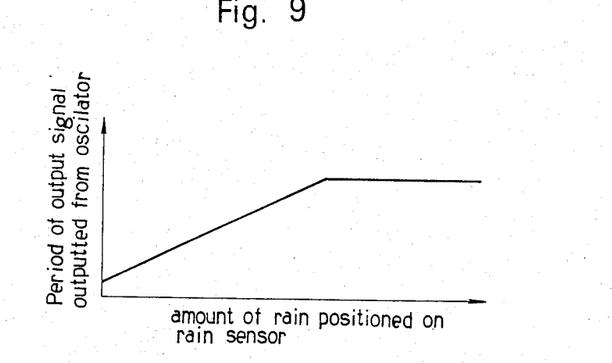
FIG. 9 is a graph showing relationship between an amount of rain positioned on the rain sensor and period of output signal outputted from the oscillator.

FIG. 8 shows an oscillator 21 which is connected to the rain sensor 100. The oscillator 21 produces an output signal which has a variable frequency from an output terminal "Sig". The variable frequency of the output signal is changed in accordance with changes on an electrostatic capacitance of the rain sensor 100. Further, the oscillator 21 has terminals "E" which are connected to an electric source, and constant voltage "5V" is applied between the terminals 92 and "E". The oscillator 21 is of a conventional resister condenser negative feed back type-oscillator which includes an operational amplifier as outputting means of the oscillator 21. When the electrostatic capacitance of the rain sensor 100 is increased in accordance with increase of the amount of rain positioned on the rain sensor 100, the variable frequency of the output signal of the oscillator 21 decreases inversely to the amount of rain positioned on the rain sensor 100. As a result, as shown in FIG. 9, the period of the output signal increases proportionally to the amount of rain positioned on the rain sensor 100. However, after the amount of rain positioned on the rain sensor 100 is more than a predetermined amount of drops of water, the period of the output signal does not increase and keeps a predetermined period.

Figure 10:
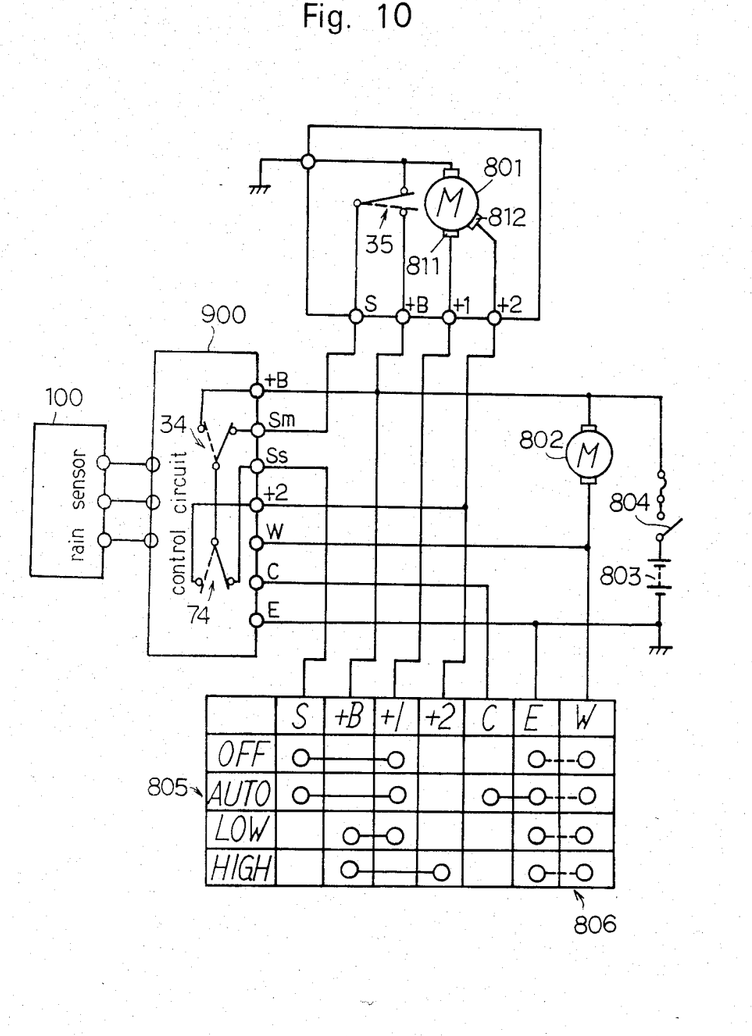
FIG. 10 is a schematic circuit illustrating an apparatus for controlling wiper, which includes the rain sensor according to the present invention.
Figure 11:
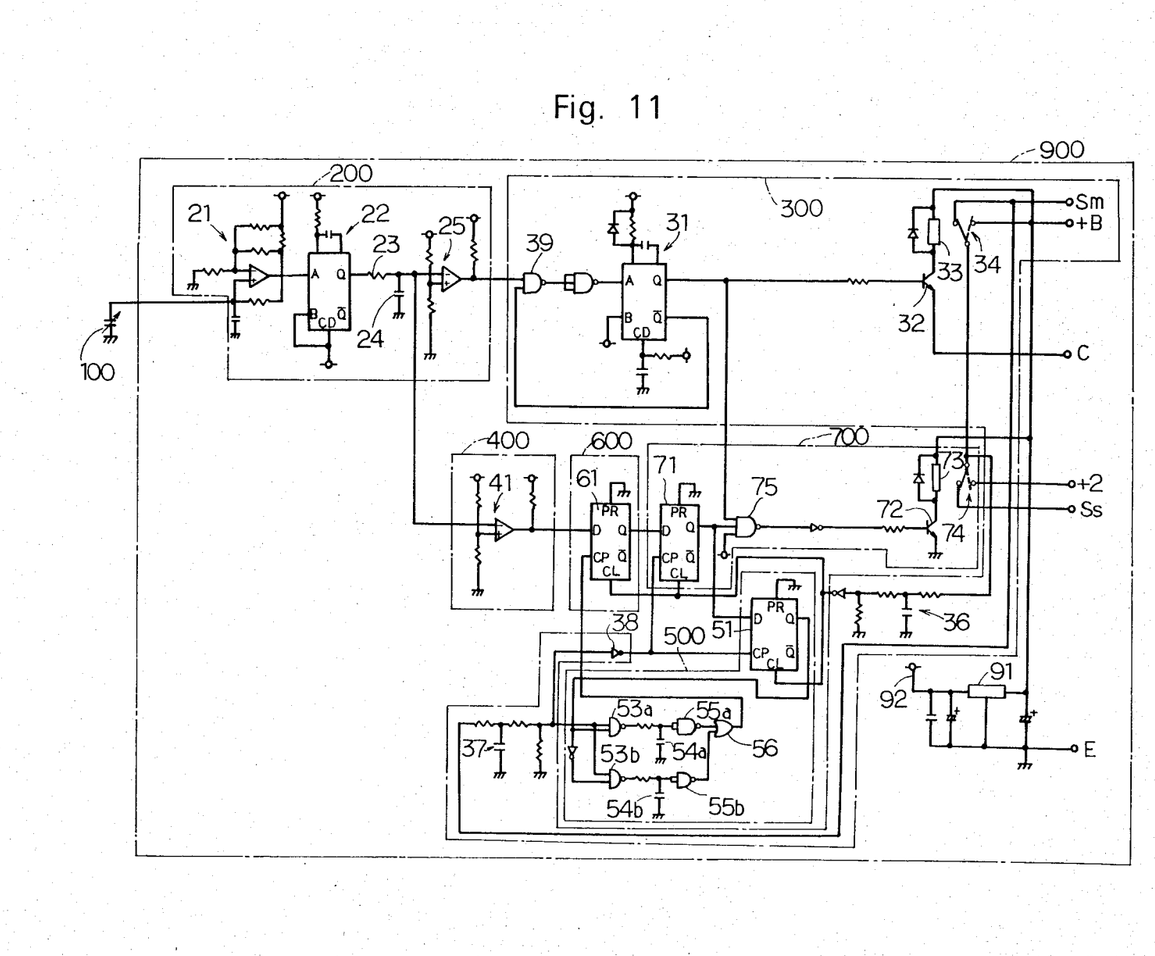
FIG. 11 is a schematic circuit illustrating a control circuit of the apparatus, shown in FIG. 10.
Figure 12:
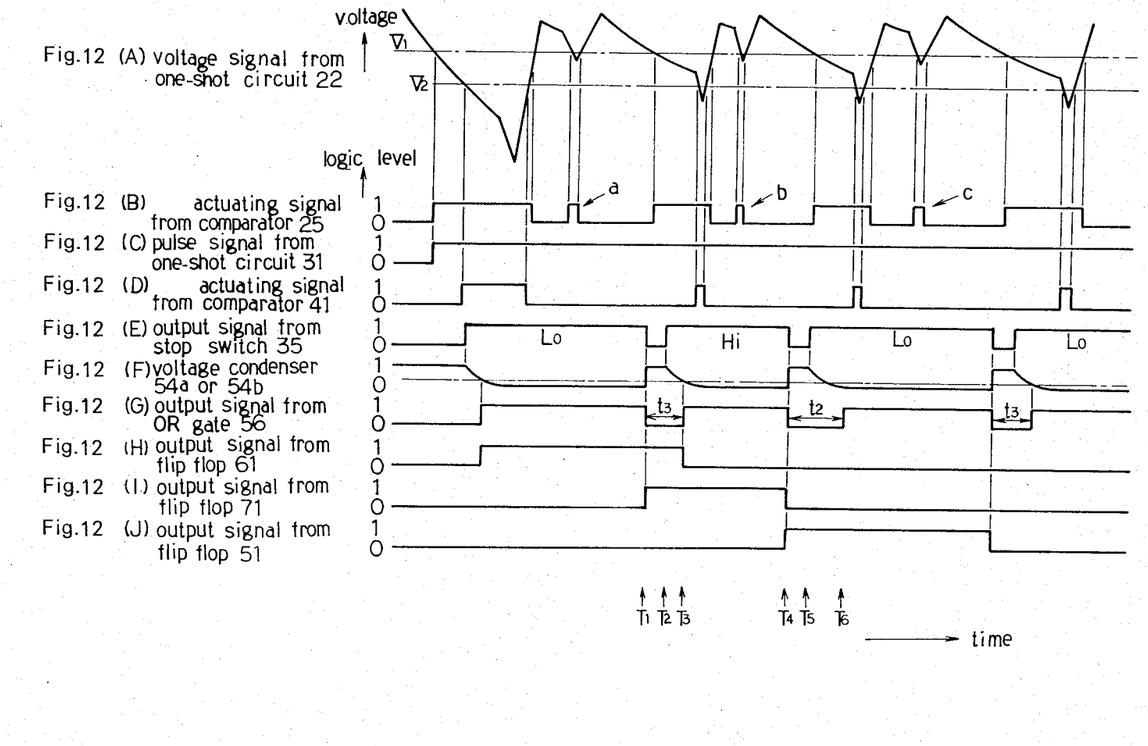

FIGS. 10 and 11 show the circuit of the apparatus for controlling a wiper, which is equipped with the rain sensor 100 according to the present invention, wherein numeral 801 indicates a motor for driving the wiper 85 and numeral 802 indicates another motor for pumping water and for emitting water from a washer nozzle (not shown in drawings) to the wiping area 80 of the windshield 84. Numeral 805 indicates a wiper switch and numeral 900 indicates a control circuit. The motor 801 is a conventional motor which can drive the wiper 85 at high or low wiping speed, and the motor 801 includes a stop switch 35. When the wiper 85 is positioned at the initial position 88 of the wiper 85, the stop switch 35 of the motor 801 is positioned at a position which is shown by a solid line in FIG. 10 and stops the movement of the wiper 85. Accordingly, when the wiper 85 is driven by the motor 801 the stop switch 35 is turned to a position which is shown by a phantom line in FIG. 10. The stop switch 35 produces logic level "1" or "0" signal as shown in FIG. 12 (E). The wiper switch 805 includes a low wiping speed switch, a high wiping speed switch, an off switch and an auto wiping speed switch.

In manual operation, when the wiper switch 805 selects the low wiping speed switch, a terminal "+B" is electrically connected to a terminal "+1", as a result, a brush 811 of the motor 801 is connected to a battery 803 through an ignition switch 804, accordingly, the motor 801 is driven at the low speed. When the wiper switch 805 selects the high wiping speed switch, the terminal "+B" is electrically connected to a terminal "+2", as a result, another brush 812 of the motor 801 is connected to the battery 803 through the ignition switch 804, accordingly, the motor 801 is driven at the high speed. When the wiper switch 805 selects the off switch, a terminal "S" is electrically connected to the terminal "+1", as a result, a moveable contact of the stop switch 35 is electrically connected to the brush 811 of the motor 801, through a first switch 34 and a second switch 74 of a control circuit 900. The first and second switches 34 and 74 are normally connected respectively to non-moveable contacts "$S_m$" and "$S_s$", as shown by the solid line in FIG. 10. When a first relay 33 is actuated, the first switch 34 is turned and connected to a non-moveable contact "+B" as shown by a phantom line in FIGS. 10 and 11, as a result, the brush 811 of the motor 801 is connected to the battery 803 through the terminals "+1" and "S" of the wiper switch 805 and the first and second switches 34 and 74 of the control circuit 900. In the same manner, when a second relay 73 is actuated, the second switch 74 is turned and connected to a non-moveable "+2" as shown by a phantom line in FIGS. 10 and 11, as a result, brush 812 of the motor 801 is connected to the battery 803 through the first and second switches 34 and 74 of the control circuit 900.

When the wiper switch 805 selects the auto wiping switch, the terminal "S" is electrically connected to the terminal "+1" and a terminal "C" is electrically connected to a terminal "E", as a result, a non-moveable contact "C" of the control circuit 900 is electrically connected to the ground and the control circuit 800 is connected to the battery 803.

Further, the wiper switch 805 includes a washer switch 806. When the washer switch 806 is turned on, the terminal "E" is electrically connected to a terminal "W" independent of selection of the wiper switch 805, as a result, motor 802 is electrically connected to the battery 803 through the ignition switch 804 and the terminal "W" is connected to the ground. Further, control circuit 900 is electrically connected to rain sensor 100.

When motor 801 is driven at high or low speed, a movable contact of the stop switch 35 is contacted non-moveable contact "+B" as shown by the phantom line in FIG. 10. In this condition, the stop switch 35 produces the logic level "1" signal, as shown in FIG. 12 (E). Accordingly, even when wiper switch 805 is operated to select the off switch during the movement of motor 801, motor 801 is continuously driven at the low speed unless wiper 85 returns to the initial position 88 of wiper 85, because brush 811 of motor 801 is connected to the battery 803 through the terminals "+1" and "S", the first and second switches 34 and 74 of the control circuit 900, the stop switch 35 and the ignition switch 804. When the wiper 85 returns to the initial position 88 of the wiper 85 and the moveable contact of the stop switch 35 is turned as shown by the solid line in FIG. 10, the movement of the motor 801 is stopped. In this condition, the stop switch 35 produces the logic level "0" signal, as shown in FIG. 12 (E).

When the wiper switch 805 selects the auto wiping switch, the control circuit 900 receives signals being in proportion to the amount of rain, which is positioned on the rain sensor 100 after the wiper 85 wipes out the rain sensor 100. Every time the detected amount of rain is equal to or more than a small predetermined amount of drops of water, the first switch 34 of the control circuit 900 is turned as shown by the phantom line in FIGS. 10 and 11 during a certain time, as a result, the motor 801 is driven at the low speed and the wiper 85 moves from the initial position 88 of the wiper 85 to an intermediate portion of the wiping area 80. Even if the first switch 34 returns to the previous position shown by the solid line in FIGS. 10 and 11 after the certain time has passed, the motor 801 is continuously driven at the low speed unless the wiper 85 moves to the apex of wiping area 80 and returns to the initial position 88 of the wiper 85, because the brush 811 of the motor 801 is connected to the battery 803 through the terminals "+1" and "S", the first and second switches 34 and 74, the stop switch 35 and the ignition switch 84.

In this condition (i.e. the wiper switch 805 selects the auto wiping switch) when the detected amount of rain becomes equal to or more than a large predetermined amount of drops of water, the first and second switch 34 and 74 of the control circuit 900 are turned as shown by the phantom line in FIGS. 10 and 11, as a result, the motor 801 is driven at the high speed.

As shown in FIG. 11, the control circuit 900 includes first comparator means 200, actuator means 300, second comparator means 400, timer means 500, memory means 600 and changing means 700. The first comparator means 200 is electrically connected to the rain sensor 100, the actuator means 300 and the second comparator means 400. When the first comparator means 200 compares the amount of rain detected by the rain sensor 100 with the small predetermined amount of drops of water and determines the detected amount of rain is equal to or greater than the small predetermined amount of drops of water, the first comparator means 200 provides the actuating signal, which has a logic level "1", to the actuator means 300. The first comparator means 200 includes an oscillator 21, one-shot circuit 22, a resister 23, a condenser 24 and a comparator 25. Oscillator 21 is of the conventional resister condenser negative feed back type-oscillator which includes an operational amplifier as outputting means of the oscillator and the oscillator 21 is connected to the rain sensor 100. When the rain sensor 100 varies its variable capacitance in proportion to amount of rain positioned on the rain sensor 100, the oscillator 21 produces an output signal. The variable frequency of the output signal is changed inversely to the amount of rain positioned on the rain sensor 100. One-shot circuit 22 receives the output signal and produces a signal which has the same period as the period of the output signal and which has a constant pulse in spite of the frequency of the output signal. And then an integration circuit, which comprises the resistor 23 and the condenser 24, receives the signal outputted from the one-shot circuit 22 and the integration circuit produces a voltage signal being in proportion to the frequency of the output signal produced by oscillator 21. Accordingly, the voltage signal is in inverse proportion to the detected amount of rain, as shown in FIG. 12 (A). The comparator 25 receives the voltage signal and the comparator 25 compares value of the voltage signal with a first predetermined value of voltage "$V_1$". When the comparator 25 determines the value of the voltage signal is equal to or less than the first predetermined value of voltage "$V_1$", the comparator 25 produces an actuating signal which has logic level "1", as shown in FIG. 12 (B). The first predetermined value of voltage "$V_1$" corresponds to the small predetermined amount of drops of water. On the other hand, when the comparator 25 determines the value of the voltage signal is less than the first predetemined value of voltage "$V_1$", comparator 25 produces another actuating signal which has logic level "0". In other words, only when the comparator means 200 determines the detected amount of rain is equal to or more than the small predetermined amount of drops water, the comparator means 200 does produce the logic level "1" actuating signal.

When the actuator means 300 receives the logic level "1" actuating signal from the comparator 200, the actuator means 300 has the moveable contact of the first switch 34 turn from the position shown by the solid line to the position shown by the phantom line in FIG. 11 and maintains the moveable contact of the first switch 34 at the phantom line position during the certain time period. Actuator means 300 includes one-shot circuit 31, a NAND gate 39, a switching transistor 32, the first relay 33 and the first switch 34. When the one-shot circuit 31 receives the logic level "1" actuating signal through the NAND gate 39, a terminal "Q" of the one-shot circuit 31 produces a pulse signal which has logic level "1" during the certain time period, as shown in FIG. 12 (C). When the switching transistor 32 receives the logic level "1" pulse signal from the one-shot circuit 31, the switching transistor 32 allows electric current to pass therethrough, as a result, the first relay 33 is actuated and the first switch 34 is turned from the solid line position to the phantom line position as shown in FIG. 11. Accordingly, when the wiper switch 805 selects the auto wiping switch, the brush 811 of the motor 801 is connected to the battery 803 through the terminals "+1" and "S" of the wiper switch 805, the second and first switches 74 and 34, and the ignition switch 84, as a result, the wiper 85 moves at the low wiping speed.

Further, the certain time period, during which the one-shot circuit 31 produces a pulse signal, is longer than a time period defined between a time when the motor 801 is actuated (i.e. the wiper 85 starts moving from the initial position 88 of the wiper 85) and a time when the stop switch 35 is turned from the solid line position to the phantom line position, as shown in FIG. 10. The NAND gate 39 receives a feed back signal produced from the one-shot circuit 31 during the certain time period, as a result, further logic level "1" actuating signal is not accepted from the first comparator means 200 to the one-shot circuit 31 of the actuator means 300 during the certain time period. In other words, when the one-shot circuit 31 outputs the logic level "1" pulse signal during the certain time period, the one-shot circuit 31 also produces the feed back signal to the NAND gate 39. As a result, the NAND gate 39 produces a signal to the one-shot circuit 31 in spite of the logic level "1" signal outputted from the first comparator means 200.

Further, when the wiper 85 wipes out more than a small predetermined amount of drops of water from the rain sensor 100, comparator 25 outputs the logic level "1" actuating signals as shown by a, b, c in FIG. 12 (B). However, when the one-shot circuit 31 produces the further logic level "1" pulse signal during the certain period, the one-shot circuit 31 does not receive the logic level "1" actuating signal from the first comparator means 200, even when more than a small predetermined amount of drops of water is passed on the rain sensor 100 with the wiper 85.

Accordingly, when the wiper 85 moves from the initial position 88 of the wiper 85 and more than a small predetermined amount of drops of water is passed on the rain sensor 100 with the wiper 85, the comparator 25 of the first comparator means 200 produces the logic level "1" actuating signal but the one-shot circuit 31 does not produce any logic level "1" pulse signal again during the certain time period. As a result, every time the one-shot circuit 31 produces the logic level "1" pulse signal, the wiper 85 moves from and returns to the initial position of the wiper 85 only once. (i.e., in the sensor according to the present invention, the wiper 85 twice wipes out twice the rain sensor 100 during the certain time period.) However, when the wiper 85 is continuously actuated as shown in FIG. 12 (C), the one-shot circuit 31 continuously produces the logic level "1" pulse signal.

Further, the actuator means 300 includes a clear circuit 36 and a low pass filter 37. The clear circuit 36 produces a clear signal when the first switch 34 is positioned as shown by the solid line in FIGS. 10 and 11 and the stop switch 35 is positioned as shown by the solid line in FIG. 10. The clear conduit 36 includes a low pass filter and an inverter and the clear signal produced from the clear circuit 36 is inputted into each terminals "CL" of delay type flip flops (i.e., delay type bistable multivibrators) 51, 61 and 71, as a result, the delay type flip flops 51, 61 and 71 are cleared. On the other hand, the low pass filter 37 prevents the signal of the stop switch 35 from chattering. The signal produced from the low pass filter 37 is inputted into the timer means 500 and the signal from the low pass filter 37 is concurrently inverted by an inverter 38 and then it is inputted into terminals "CP" of the delay type flip-flops 51 and 71.

Furthermore, the voltage signal produced by the condenser 24 of the first comparator means 200 is inputted into the second comparator means 200 and inputted into the second comparator means 400. The second comparator means 400 includes a comparator 41 which outputs an actuating signal which has logic level "1", when the comparator 41 determines the voltage signal outputted from the condenser 24 is equal to or less than a second predetermined value of voltage "V$_2$", as shown in FIG. 12 (D). (i.e., when the comparator means 400 determines the detected amount of rain is equal to or greater than the large predetermined amount of drops of water, the comparator means 400 outputs the second actuating signal which has logic level "1".)

The memory means 600 includes the delay type flip flop 61 and the logic level "1" actuating signal is inputted into a terminal "D" of the flip flop 61 of the memory means 600. When a terminal "CP" of the flip flop 61 receives a clock signal which has logic level "1" and the logic level "1" second actuating signal is inputted in the terminal "D" of the flip-flop 61 of the memory means 600, the flip flop 61 produces an output signal, which has logic level "1", from a terminal "Q" thereof.

Changing means 700 includes the delay type flip flop 71, a NAND gate 75, a switching transistor 72, the second relay 73 and the second switch 74. Terminal "D" of the flip flop 71 receives the output signal produced by the flip flop 61 of the memory means 600, when a terminal "CP" of the flip flop 71 receives the signal, which has logic level "1", from the low pass filter 37 through the inverter 38. The flip flop 71 then memorizes the output signal produced by flip flop 61 and produces a signal, which has logic level "1", from a terminal "Q" of the flip flop 71. When the NAND gate 75 receives both the logic level "1" signals produced by one-shot circuit 31 and flip flop 71, the logic level "1" signal outputted from the flip flop 71 is inputted to switching transistor 72 through the NAND gate 75. As a result, the electric current passes through the switching transistor 72 and the second relay 73 is actuated. Accordingly, the second switch 74 is turned from the position shown by the solid line to the position shown by the phantom line in FIG. 11.

As shown in FIG. 10, when the first switch 34 and the second switch 74 are turned to the position shown by the phantom line, the battery 803 is connected to brush 812 of the motor 801 through the ignition switch 804, the first and second switches 34 and 74. As a result, the motor 801 is driven at the high speed.

On the other hand, if NAND gate 75 does not receive both the signals produced by flip flop 71 and the one-shot circuit 31, the NAND gate 75 closes and switching transistor 72 does not receive any signal.

Timer means 500 produces a clock signal, which has logic level "0", during a long or short time period "t$_2$" or "t$_3$" after the wiper 85 returns to the initial position 88. When the wiper 85 was previously driven at the high wiping speed, timer 500 produces the logic level "0" clock signal during the long time period "t$_2$" after the wiper 85 returns to the initial position 88. On the other hand, if wiper 85 was previously driven at the low wiping speed, the time means 500 outputs the logic level "0" clock signal during the short time period "t$_3$" after the wiper 85 returns to the initial position 88. Further, the time period, which is defined between the time when the wiper 85 wipes out the rain sensor 100 and the time when the wiper 85 returns to the initial position 88 of the wiper 85, depends on the low or high wiping speed (i.e., when the wiper 85 is driven at the high wiping speed, the time period "t$_{(hi)}$" is rather short. On the other hand, if the wiper 85 is driven at the low wiping speed, the time period "t$_{(low)}$" is rather long).

To detect the amount of rain positioned on the rain sensor 100 during a predetermined constant time period in spite of the different wiping speed, and to compare the detected amount of rain with the large predetermined amount of drops of water, a time period ("t$_{(hi)}$"+"t$_2$") and a time period ("t$_{(Low)}$"+"t$_3$") are determined to be the substantially same as a predetermined constant time period. Therefore, the flip flop 61 of the memory means 600 memorizes the logic level "1" second actuating signal outputted from the second comparator means 400 and reproduces the memorized second output signal when the predetermined constant time period has passed after the wiper 85 had wiped out the rain sensor 100. (e.g., When the wiper 85 has wiped out the rain sensor 100 at the high wiping speed and when the second comparator means 400 determines the detected amount of rain during the predetermined constant time period after the wiper 85 wipes out the rain sensor 100 is equal to or greater than the large predetermined amount of drops of water, the memory means 600 reproduces the logic level "1" memorized second actuating signal at the time when the time period "$t_{(hi)}$"+"$t_2$" has passed after the wiper 85 has wiped out rain sensor 100. On the other hand, when the wiper 85 has wiped out the rain sensor 100 at the low wiping speed and when the second comparator means 400 determines the detected amount of rain during the predetermined constant time period after the wiper 85 wipes out the rain sensor 100 is equal to or greater than the large predetermined amount of drops of water, the memory means 600 reproduces the logic level "1" memorized second actuating signal at the time when the time period "$t_{(Low)}$"+"$t_3$" has passed after the wiper 85 had wiped out the rain sensor 100).

The timer means 500 includes the delay type flip flop 51, NAND gates 53a and 53b, condensers 54a and 54b, inverters 55a and 55b and an OR gate 56. The delay type flip flop 51 memorizes either logic level "1" or logic level "0" change output signal which is produced by the terminal "Q" of the flip-flop 71 of the changing means 700 and outputs logic level "1" or logic level "0" signal to the NAND gates 53a and 53b at the time the moveable contact of the stop switch 35 is turned to the solid line position shown in FIG. 10, (i.e. when the wiper 85 returns to the initial position 88). When the memorized signal has logic level "1", the NAND gate 53a opens and the NAND gate 53b closes. On the other hand, if the memorized signal has logic level "0", the NAND gate 53a closes and the NAND gate 53b opens. The signal is inputted from the low pass filter 37 to the NAND gates 53a and 53b. Condenser 54a and the inverter 55a are connected to the output side of the NAND gate 53a and the NAND gate 53a, the condenser 54a and the inverter 55a produce the long time period signal "$t_2$" which has logic level "0". On the other hand, the condenser 54b and the inverter 55b are connected to the output side of the NAND gate 53b and the NAND gate 53b. Condenser 54b and the inverter 55b produce the short time period signal "$t_3$" which has logic level "0". The signals produced by inverter 55a or 55b are inputted to the OR gate 56 and a terminal "CP" of the flip flop 61.

Accordingly, when the wiper 85 moves from the initial position 88 of the wiper 85 and logic level "1" signal which is produced by stop switch 35, which is shown in FIG. 12 (E), is inputted to either NAND gate 53a or 53b through the low pass filter 37, either condenser 54a or 54b discharges, as shown in FIG. 12(F), in accordance with the logic level of the output signal from the flip flop 51. More particularly, while the flip flop 51 produces the output signal which has the logic level "0", the condenser 54b starts to discharge at a time when the logic level "1" output signal is outputted from the stop switch 35 through the low pass filter 37, (e.g., the stop switch 35 is turned from the position shown by the solid line to the position shown by the phantom line in FIG. 10), and the condenser 54b discharges after the logic level "1" output signal is produced by stop switch 35. Accordingly, the inverter 55b produces a signal, which has logic level "1", to a terminal "CP" of the flip flop 61 through the OR gate 56 at the short time period "$t_3$" after the wiper 85 returns to the initial position 88 of the wiper 85, as shown in FIG. 12(G).

On the other hand, while the flip flop 51 produces the output signal which has the logic level "1", the condenser 54a starts to discharge at a time when the logic level "1" output signal is produced by the stop switch 35 through the low pass filter 37, and the condenser 54a discharges after the logic level "1" output signal is produced by the stop switch 35. Accordingly, the inverter 55a outputs a signal, which has logic level "1" to the terminal "CP" of the flip flop 61 through the OR gate 56 at the long time period "$t_2$" after the wiper 85 returns to the initial position 88 of the wiper 85, as shown in FIG. 12(G).

In FIG. 11, a numeral 91 indicates a voltage regulator which is connected between terminals "+B" and "E" of the control circuit 900. When the ignition switch 804 is turned on and the voltage of the battery 803 is applied between the terminals "+B" and "E" of the control circuit 900, an output terminal 92 outputs a constant voltage (i.e., 5 V) which is supplied to all means of the control circuit 900.

Further, the control circuit 900 includes a delay circuit (not shown in drawings) which supplies the current to the first relay 33 at a few seconds after the washer switch 806 is turned on, as a result, the first switch 34 is turned from the position shown by the solid line to the position shown by the phantom line in FIG. 11 and then the brush 811 of the motor 801 is connected to the battery 803 through the ignition switch 84, the first and second switch 34 and 74 and the terminals "S" and "+1" of the wiper switch 805.

The operation of the apparatus for controlling wiper disclosed in FIGS. 10 through 12 is found in U.S. patent application Ser. No. 814,801 filed Dec. 30, 1985, entitled "An apparatus and a method for controlling wiper", and assigned to the same assignee as the present invention.

As described herein, the present invention overcomes the shortcomings of the known art by providing a transparent sensor for detecting the amount of rain positioned thereon.

While the present invention has been described in its preferred embodiment, it is to be understood that the invention is not limited thereto, and may be otherwise embodied within the scope of the following claims.

What is claimed is:

1. A sensor for detecting an amount of rain comprising:

a first conductor member being made of transparent material, the first conductor member including a plurality of first projections, each of the plurality of first projections being spaced from the other of the plurality of first projections;

a second conductor member being made of transparent material, the second conductor member including a plurality of second projections, each of the plurality second projections being spaced from the other of the plurality of second projections, at least one of the plurality of second projections being inserted between two of the plurality of first projections of said first conductor member with a clearance, said first conductor member being insulted electrically from said second conductor member by the clearance; and a first insulating member being mounted on said first and second conductor members, said first insulating member being made from a first transparent material.

2. A sensor for detecting an amount of rain of claim 1, further comprising a base insulating member being made of transparent material, said first and second conductor members being mounted on said base insulating member.

3. The sensor for detecting an amount of rain of claim 2, wherein said first insulating member is mounted on said first and second conductor members and said base insulating member being defined between said first and second conductor members.

4. A sensor for detecting an amount of rain of claim 3, further comprising an anti-reflecting member being mounted on said first insulating member, said anti-reflecting member being made from a second transparent material.

5. The sensor for detecting an amount of rain of claim 4, wherein the first transparent material of said first insulating member is selected from the group consisting of Alumina, Zirconia and Silica.

6. The sensor for detecting an amount of rain of claim 5, wherein the second transparent material of said anti-reflecting member is selected from the group consisting of Alumina, Zirconia and Silica.

7. The sensor for detecting an amount of rain of claim 6, wherein a combination of the transparent material of said first insulating member with the second transparent material of said anti-reflecting member is selected from the group consisting of a first combination of Alumina with Silica, a second combination of Zirconia with Alumina, a third combination of Zirconia with Silica and a fourth combination of Silica with Alumina.

8. The sensor for detecting an amount of rain of claim 4, wherein said anti-reflecting member is fixed to said first insulating member by a method being selected from spattering, vacuum evaporation and ion plating.

9. The sensor for detecting an amount of rain of claim 3, wherein said first conductor member includes a plurality of first wide portions and said second conductor member includes a plurality of second wide portions, the plurality of first projections extending from the plurality of first wide portions, the plurality of second projections extending from the plurality of second wide portions, the first and second wide portions defining a plurality of groups of first and second projections.

10. The sensor for detecting an amount of rain of claim 3, wherein said first insulating member is fixed to said first and second conductor members and said base insulating member by a method being selected from spattering, vacuum evaporation and ion plating.

11. The sensor for detecting an amount of rain of claim 2, wherein said base insulating member is a windshield.

12. The sensor for detecting an amount of rain of claim 2, wherein said first and second conductor members are fixed to said base insulating member by a method being selected from spattering, vacuum evaporation and ion plating.

13. The sensor for detecting an amount of rain of claim 1, wherein said first and second conductor members are made from ITO film.

14. A sensor for detecting amount of rain comprising:
a base insulating member being made from transparent material;
a first conductor member being made from transparent material, the first conductor member being fixed to said base insulating member, the first conductor member including a plurality of first projections, each of the plurality of first projections being spaced from the other of the plurality of first projections;
a second conductor member being made from transparent material, the second conductor member being fixed to said base insulating member, the second member including a plurality of second projections, each of the plurality of second projections being spaced from the other of the plurality of second projections, at least one of the plurality of second projections being inserted between two of the plurality of first projections of said first conductor member with a clearance, said first conductor member being insulated electrically from said second conductor member by the clearance; and
a first insulating member being fixed to said first and second conductor members and said base insulating member being defined between said first and second conductor members, said a first insulating member being made from a first transparent material.

15. The sensor for detecting an amount of rain of claim 14, wherein said first conductor member includes a plurality of first wide portions and said second conductor member includes a plurality of second wide portions, the plurality of first projections extending from the plurality of first wide portions, the plurality of second projections extending from the plurality of second wide portions, the first and second wide portions defining a plurality of groups of first and second projections.

16. A sensor for detecting an amount of rain of claim 15, further comprising an anti-reflecting member being mounted on said first insulating member, said anti-reflecting member being made from a second transparent material.

17. A sensor for detecting an amount of rain comprising:
a windshield being made from transparent material;
a first conductor member being made from ITO film, the first conductor member being fixed to said windshield, the first conductor member including a plurality of first projections, each of the plurality of first projections being spaced from the other of the plurality of first projections;
a second conductor member being made from ITO film, the second conductor member being fixed to said windshield, the second conductor member including a plurality of second projections, each of the plurality of second projections being spaced from the other of the plurality of second projections, at least one of the plurality of second projections being inserted between two of the plurality of first projections of said first conductor member with a clearance, said first conductor member being insulated electrically from said second conductor member by the clearance; and
a first insulating member being fixed to said first and second conductor members and to said windshield being defined between said first and second conductor members, said first insulating member being made from a first transparent material.

18. A sensor for detecting an amount of rain of claim 17, further comprising an anti-reflecting member being mounted on said first insulating member, said anti-reflecting member being made from a second transparent material.

19. The sensor for detecting an amount of rain of claim 18, wherein said first conductor member includes a plurality of first wide portions and said second conductor member includes a plurality of second wide portions, the plurality of first projections extending from the plurality of first wide portions, the plurality of second projections extending the plurality of second wide portions, the first and second wide portions defining a plurality of groups of first and second projections.

20. The sensor for detecting an amount of rain of claim 19, wherein the first transparent material of said first insulating member is selected from the group consisting of Alumina, Zirconia and Silica.

* * * * *